United States Patent [19]

Jelenko, III

[11] 4,051,257

[45] Sept. 27, 1977

[54] TOPICAL VETERINARY DERMATOLOGICAL MEDICAMENT

[76] Inventor: Carl Jelenko, III, Medical College of Ga., Augusta, Ga. 30902

[21] Appl. No.: 628,143

[22] Filed: Nov. 3, 1975

Related U.S. Application Data

[63] Continuation-in-part of Ser. No. 432,216, Jan. 10, 1974, Pat. No. 3,920,848.

[51] Int. Cl.² .............................................. A61K 31/23
[52] U.S. Cl. ................................................... 424/312
[58] Field of Search .............................. 424/312, 365

[56] References Cited

U.S. PATENT DOCUMENTS

| 3,198,704 | 8/1965 | Roy | 424/312 |
| 3,676,472 | 7/1972 | Ziluken et al. | 424/312 |

OTHER PUBLICATIONS

American Perfumer, Jan. 1962, vol. 77, #1, (1962) pp. 23–26.

Drug and Cosmetic Industry, Mar. 1960: 86, 3 pp. 330, 331 and 393.

Primary Examiner—Frederick E. Waddell
Attorney, Agent, or Firm—John S. Roberts, Jr.

[57] ABSTRACT

A method of treating dermatoses with ethyl linoleate is provided.

5 Claims, No Drawings

TOPICAL VETERINARY DERMATOLOGICAL MEDICAMENT

This application is a continuation-in-part of application Ser. No. 432,216 filed Jan. 10, 1974, by Carl Jelenko, III, entitled "A Topical Agent for Alleviation of Full Thickness Burns in Mammals" [now U.S. Pat. No. 3,920,848].

A topical method and preparation for the relief of non-bacterial dermatoses or dermatides in animals for veterinary use is presented and the alleviation of these conditions in the skin of animals excludes consideration of burns, which have an additional quality of destruction of the skin. The basic active ingredient utilized is ethyl linoleate, defined specifically as the active isomer which is ethyl-cis,cis,(9,12)-octadecadienoate. For veterinary use a preferred dosage on such animals as dogs, cats, and horses is 25 mg/kg of body weight, which is equivalent to 0.01 ml/cm$^2$. Thus, one drop, which is 0.1 ml, would be effective as 15 mg/kg of body weight and a range up to 75 mg/kg of body weight, or 5 drops, is indicated. An exemplary dosage based on body weight for a 10-pound dog or cat (4.55 kgs) would utilize two drops, which would be approximately 25 mg/kg as a minimum dosage. It is often more convenient to express the dosage in square centimeters or square inches of the area to be covered, and for coverage on hairless skin it has been found that a dosage of one drop is preferred for an upper coverage range of from 16 to 36 in.$^2$ of area. Additionally, one drop may be utilized for an area up to 36 in.$^2$ Thus, one drop is usually sufficient for a minimum coverage of an average affected area for dermatoses.

The range given is based on a suggested preferred dosage to be repeated as needed at the end of 5-7 days after the initial dose. In some cases, in prolonged treatment, a sustaining or maintenance dose is given which may be repeated for a period up to 6 months and beyond where the interval between dosages is biweekly to monthly.

A preferred composition for treatment is hELate-V, which contains as active ingredients 73% ethyl linoleate combined with minor amounts of anti-oxidants α-tocopherol, d,l-histidine, and tertiary butyl hydroquinone, together with a stabilizer or filler such as Tween-80, and the inactive ingredients include additional ethyl esters primarily ethyl oleate together with ethyl palmitate and ethyl stearate (C. Jelenko, Medical College of Georgia, Augusta,).

Other conventional food grade anti-oxidants may be substituted for one or more of the preferred anti-oxidants noted above. The skin conditions amenable to treatment include various dermatides and exclude staphyloccal infections and burns. These skin conditions may be termed non-bacterial dermatoses and the present topical remedy finds a field of use in a wide range of such disorders in the veterinary field.

The present medication for veterinary use is topical and its purpose is to utilize the liquid active isomer of ethyl linoleate, specifically ethyl-cis,cis,(9,12)-octadecadienoate, as the active ingredient for relieving dermatological difficulties in such animals as horses, dogs, and cats.

The prior art relating to ethyl linoleate is believed to be as follows.

Zilliken et al. U.S. Pat. No. 3,676,472 relates to staphylococcal infections and prophylactic treatment thereof as well as injection but does not deal with a topical therapeutic treatment. Zilliken notes that mammals may be protected in a prophylactic manner against staphylococcal infections.

The present invention, as distinguished from Zilliken, does not deal with staphylococcal infections.

The coverage from a veterinary sense engendered by the present application is to cover applications to major animals which would be treated, such as horses, dogs, cats, etc.

This topical remedy for animal treatment is designed to alleviate conditions in the skin of animals which excludes consideration of burns, which have the additional quality of destruction of skin. Among others, the remedy is for the relief of non-bacterial dermatoses or dermatides and is effective in a wide range of dermatological conditions such as granulamatous lesions with or without serum weeping in the skin areas, contact dermatides, licking disease, eosinophilic granuloma, erythema, and pruritus. A recent monograph which defines non-bacterial dermatoses is "The Skin" by Allen, 2nd edition, 1967, published by Grune and Stratten.

The dosage recommended is 1 drop (15 mg/kg) to 5 drops (75 mg/kg) where the kilogram unit refers to body weight of the animal. This preferred dosage may be repeated as needed at the end of 5-7 days after initial dose. An alternative modus of expressing dosage based on skin coverage is a preferred level of from 1 drop per 16 in.$^2$ to 1 drop per 36 in.$^2$ based upon hairless skin. Additionally, to effectively treat small conditions, the dosage may be 1 drop for any area up to 36 in.$^2$ In discussion of dosage it should be mentioned that, whereas the recommended dosage is to a second dose 5-7 days, in some cases it has been found that an alternative successful therapy was to utilize the medication on several successive days. In the animal cases utilized, this caused no untowards side effects since the margin of safety for toxicity is large and is about 60:1 of the recommended initial dose of 25 mg/kg of body weight. Ordinarily it has been found that the hELate applied once at an interval of 5-7 days is recommended due to the efficacy of the formulation in relieving skin disorders; however, it is possible as shown in Examples 4 and 5 to treat the animal by successive day treatments and even multiple treatment per diem. The large margin of safety in toxicity makes it possible for the animal to be treated with a substantial dosage in excess of the recommended dosage with safety and freedom from side effects. In such a maintenance regimen the hELate-V or other ethyl linoleate preparation may be applied topically at the preferred dosage once a month up to a period of 6 months and beyond where the time span varies from biweekly to monthly.

A preferred composition for dermatological treatment is hELate-V, which contains as active ingredients 73% ethyl linoleate combined with minor amounts of anti-oxidants α-tocopherol, d,l-histidine and tertiary butyl hydroquinone, together with a stabilizer or filler such as Tween-80, and the inactive ingredients include additional ethyl esters primarily ethyl oleate together with ethyl palmitate and ethyl stearate (C. Jelenko, Medical College of Georgia, Augusta, Ga). Specifically hELate-V is as follows:

|  | Grams |
|---|---|
| Active Ingredient: | |
| Ethyl linoleate | 35.95 |
| Anti-oxidants: | |
| α-tocopherol | 0.43 |

| | Grams |
|---|---|
| d,l-histidine | 0.78 |
| Tertiary butyl hydroquinone | 0.0002 |
| Stabilizer: | |
| Tween-80 | 0.1539 |
| Inactive Ingredients: | |
| Ethyl oleate | 10.07 |
| Ethyl palmitate and ethyl stearate | 1.92 |

In this composition or similar formulations, the ethyl linoleate is utilized as the active isomer form, which is ethyl-cis,cis,(9,12)-octadecadienoate. Other conventional food grade anti-oxidants may be substituted for one or more of the anti-oxidants noted above. Such food grade anti-oxidants may be selected from the following list as set out in Ralph G. Harry, The Principles and Practice of Modern Cosmetics, Volume 1, Modern Cosmeticology, page 617, 1962:

Guaiacum resin
Nordihydroguaiaretic acid
Tocopherols
Lecithin
Butylated hydroxyanisole
Butylated hydroxytoluene
Trihydroxybutyrophenone
Ascorbic palmitate
Monoisopropyl citrate
Thiodipropionic acid
Dilauryl thiodipropionate
Distearyl thiodipropionate

EXAMPLE 1

A canine male Dachshund, 7 years old, had symptoms of skin inflammation of the groin area with itching, serum discharge, and erythema, which was probably an allergic manifestation related to hot, humid environment and summer allergies.

hELate-V (which is ethyl linoleate--EL 75%, d,l-histidine 0.2 mg/g EL, α-tocopherol 0.1 mg/g EL, tertiary butyl hydroquinone 5 ppm) was applied topically one time to the affected area. One drop was used, calculated as 10 drops per cc of hELate, and an area of 16 in.$^2$ was treated. The itching subsided within one hour and the entire effected area returned to normal within 24 hours.

EXAMPLE 2

A feline spayed female Domestic Short Hair, 5 years old, was the subject. This animal had long standing intermittent problems of alopecic itching, serous discharge, and resultant formation of crusts, dorsal and anterior to the ears. Medically this could be viewed as inflamed erythematous, which consisted of a crusty area around the ears (bilateral) with obvious pruritus probably related to stress and changes in environment. The area effected was about 4 in.$^2$ in area and the treatment consisted of 1 drop of hELate-V applied by Q-tip to the affected area. The results were that the pruritus decreased markedly within a few hours. The animal continued to scratch occasionally but this appeared to be more by habit rather than related to the local lesion. The lesion healed completely within 2 days; however, the hair growth remained more sparse than normal.

EXAMPLE 3

Maintenance Dosage

The subject was a feline male Domestic Short Hair, 7 years old, who had long standing (4 years) granulamatous lesions of the entire posterior aspects of both rear legs. Serum discharge was profuse with resulting crusts. This cat had been treated for 4 years by many different medications including tattooing and the application topically, orally, and parenterally of many medications including antibiotics, sulfur ointments, and folk medicines such comfree leaf, with no effect whatever. The cat licked the lesions consistently and thus removed all topical medication as fast as it was applied. Use of a restraining collar was of little help. The diagnosis was eosinophilic granuloma. As treatment, hELate-V was applied topically once a month for 4 months and biweekly for 2 months, using 1 drop per leg and calculating 5 in.$^2$ of surface area per leg. The results were that within a few days healing was in progress and within one month the left leg was about half healed, while the right leg was about 10% healed. Within 4 months the left leg was completely healed and the right leg was over 50% healed. After 6 months the left leg remained healed and a maintenance application of hELate was continued. It was found that discontinuing treatment results in return of the granulomas within 2–4 weeks. After 6 months the right leg was healed to about 90%. The cat continued to lick both legs.

EXAMPLE 4

Comparative Surplus Dosing

The subject was a canine male poodle 11 years old, who had front feet itching with infrequent bleeding and chewing of feet. The interdigital skin as red, swollen and serum encrusted. The skin under the feet adjacent to the pads also was inflamed. hELate-V was applied topically to the effected areas for three consecutive days. The dosage utilized was one drop per foot or calculated at 3–4 square inches per foot.

The results were that itching significantly relieved on day 2 and the chewing of feet abated after day 3. By day 4 the patient was comfortable and the inflammation was minimal with tissue repair evident.

EXAMPLE 5

Comparative Surplus Dosing

The subject was a feline male Domestic Short Hair, 4 years old, with symptoms of scratching at the right ear with resulting bleeding. The cat had an abraded serum weeping area at the base of the ear. The treatment comprised clipping the area, cleansing it, and applying hELate-V topically to the entire lesion and adjacent area twice a day for 2 days. The area estimated was 2 in.$^2$ and 1 drop was applied as dosage. A collar device was applied to prevent the patient from further self-mutilation and the animal was confined to owner's home.

The animal was seen on day 5 and it was noted that the lesion had healed and was dry.

I claim:

1. A method of relieving non-bacterial dermatoses selected from one member of the group consisting of contact dermatitis, licking disease, erythema, and pruritis in verterinary animals which consists of applying to such affected dermatoses on an animal an effective amount of ethyl-cis,cis-(9,12)-octadecadienoate in a dosage of one drop to cover an area up to 36 square inches.

2. The method of claim 1 wherein the area covered is 16–36 square inches.

3. The method of claim 1 wherein the ethylcis,-cis,(9,12)-octadecadienoate is applied in a dosage of 15 mg/kg of body weight to 75 mg/kg of body weight.

4. The method of claim 3 wherein the dosage is about 25 mg/kg of body weight.

5. A method of sustained maintenance to alleviate the symptoms of non-bacterial dermatoses selected from one member of the group consisting of contact dermatitis, licking disease, erythema, and pruritis in a veterinary animal which consists of applying a dosage of ethyl linoleate ranging from 15 mg/kg to 75 mg/kg of body weight of said animal to the affected dermatoses on an aminal and repeating said dosage at intervals ranging from about biweekly to monthly.

* * * * *